United States Patent
Minakami et al.

(10) Patent No.: US 11,071,734 B2
(45) Date of Patent: Jul. 27, 2021

(54) TABLETED MEDICINAL COMPOSITION COMPRISING NALFURAFINE

(71) Applicant: Toray Industries, Inc., Tokyo (JP)

(72) Inventors: Satoshi Minakami, Kamakura (JP); Suguru Takaki, Kamakura (JP); Kotoe Ohta, Kamakura (JP); Yasuhide Horiuchi, Mishima (JP)

(73) Assignee: Toray Industries, Inc., Tokyo (JP)

( * ) Notice: Subject to any disclaimer, the term of this patent is extended or adjusted under 35 U.S.C. 154(b) by 6 days.

(21) Appl. No.: 16/497,717

(22) PCT Filed: Mar. 30, 2018

(86) PCT No.: PCT/JP2018/013684
§ 371 (c)(1),
(2) Date: Sep. 25, 2019

(87) PCT Pub. No.: WO2018/181920
PCT Pub. Date: Oct. 4, 2018

(65) Prior Publication Data
US 2021/0000817 A1    Jan. 7, 2021

(30) Foreign Application Priority Data
Mar. 31, 2017    (JP) ............................. JP2017-070165

(51) Int. Cl.
*A61K 31/485*    (2006.01)
*A61K 9/20*    (2006.01)

(52) U.S. Cl.
CPC .......... *A61K 31/485* (2013.01); *A61K 9/2018* (2013.01); *A61K 9/2054* (2013.01)

(58) Field of Classification Search
CPC ... A61K 31/485; A61K 9/2018; A61K 9/2054
(Continued)

(56) References Cited

U.S. PATENT DOCUMENTS

2001/0004637 A1    6/2001    Hanamura et al.
2010/0120815 A1*   5/2010    Takaki ................. A61K 9/2054
                                                               514/282
(Continued)

FOREIGN PATENT DOCUMENTS

WO    95/20380 A1    8/1995
WO    99/02158 A1    1/1999
(Continued)

OTHER PUBLICATIONS

*The Japanese Pharmacopoeia*, Fifteenth Edition, 2006, Official Monographs, "Lactose Hydrate" [see English summary at pp. 803-804], and "Hydroxypropylcellulose" [see English summary at pp. 736-738].
(Continued)

*Primary Examiner* — Taylor V Oh
(74) *Attorney, Agent, or Firm* — DLA Piper LLP (US)

(57) ABSTRACT

A tableted pharmaceutical composition contains nalfurafine or a pharmaceutically acceptable acid addition salt thereof and is excellent in formability and quality control of related substances. The tableted pharmaceutical composition includes nalfurafine or a pharmaceutically acceptable acid addition salt thereof, a binder component, and a carrier, wherein the above mentioned nalfurafine or a pharmaceutically acceptable acid addition salt thereof is contained in an amount of 0.1 to 10 μg, and the weight of the above mentioned binder component is 100,000 to 2,000,000 weight % based on the weight of the above mentioned nalfurafine or a pharmaceutically acceptable acid addition salt thereof and 5 to 20 weight % based on the total weight of the resulting pharmaceutical composition, or 20,000 to 500,000 weight % and 1 to 5 weight % based on the total weight of the resulting pharmaceutical composition.

19 Claims, 3 Drawing Sheets

(58) Field of Classification Search
USPC .......................................................... 514/282
See application file for complete search history.

(56) References Cited

U.S. PATENT DOCUMENTS

2012/0058186 A1    3/2012  Takaki et al.
2012/0114752 A1    5/2012  Ohta et al.

FOREIGN PATENT DOCUMENTS

WO      2008/133330 A1     11/2008
WO      2010/047381 A1      4/2010
WO      2010/113841 A1     10/2010

OTHER PUBLICATIONS

*Japanese Pharmaceutical Excipients Directory* 2016, edited by the Japan Pharmaceutical Excipients Council, Yakuji Nippo Ltd., Feb. 18, 2016, 10 pages, including a partial English translation.
The Extended European Search Report dated Nov. 12, 2020, of counterpart European Application No. 18775647.3.
ICH-Q3 Guideline for Impurities in New Drug Products, 2006, pp. 1-12, retrieved from https://www.ich.org/products/guidelines/quality/article/quality-guidelines.html.
Parasrampuria, J. et al., "Quantitation of Famotidine in Pharmaceutical Dosage Forms Using High-Performance Liquid Chromatography," *Drug Development and Industrial Pharmacy*, 1989, vol. 15, No. 12, pp. 1989-1997, abstract only.

* cited by examiner

TABLETED MEDICINAL COMPOSITION COMPRISING NALFURAFINE

TECHNICAL FIELD

This disclosure relates to a highly pure pharmaceutical composition which comprises as an active ingredient nalfurafine or a pharmaceutically acceptable acid addition salt thereof, which has a handleable formability, and which facilitates the quality control of related substances.

BACKGROUND

Solid pharmaceutical formulations are required to have certain formability so that the form does not change and powdery dust or the like is not produced at the time of production or handling at a medical site. Especially, in an active ingredient whose weight in one tablet is extremely low and which is highly active and shows medicinal effect with a low content, it is important to provide certain formability to suppress the exposure to medical workers caused by the production of powdery dust or to suppress the contamination in a single package with other agents due to the powdery dust.

In addition, as another aspect of the quality control, the control of related substances is listed as an important quality control item to reduce the risk of the onset of side effects caused by the production of related substances derived from the active ingredient. The threshold value to be controlled of related substances is indeed defined in detail in the International Council on Harmonization of Technical Requirements for Registration of Pharmaceuticals for Human Use, called ICH (ICH-Q3 Guideline for Impurities in New Drug Products). However, for the formulation of an active ingredient which is highly active and is contained in a low amount in a single tablet dose, it is in general extremely difficult to provide a highly pure solid formulation which facilitates the control of related substances because pharmaceutical additives which constitute the formulation interfere with the analysis of the active ingredient.

The active ingredient, nalfurafine or a pharmaceutically acceptable acid addition salt thereof, is a selective opioid κ receptor agonist that exhibits a potent antipruritic action against itch of central origin, and is available on the market as a soft capsule. The content of the active ingredient is 2.5 μg per tablet and, thus, it is an active ingredient which is highly active with a very low content.

WO 99/002158 describes an injection solution, a soft capsule, a tablet and the like which contain nalfurafine hydrochloride. That patent describes that the stability is improved by adding to the nalfurafine hydrochloride a substance selected from a specific antioxidant, a synergist, a sugar or a surfactant.

WO 08/133330 discloses a solid formulation of nalfurafine hydrochloride which contains mannitol and low-substituted hydroxypropyl cellulose and which has excellent storage stability. That patent describes a step of preparing a granulated product by spraying on mannitol a binder solution in which nalfurafine hydrochloride is dissolved. For the binder component, it is described that the addition of a polymer such as hydroxypropyl cellulose or hydroxypropyl methyl cellulose improves the stability.

WO 10/047381 discloses a tablet of nalfurafine hydrochloride which contains mannitol and crospovidone or sodium carboxymethyl starch and which is excellent in storage stability and disintegration in the oral cavity. That patent describes a step of preparing a granulated product by spraying a binder solution in which nalfurafine hydrochloride is dissolved on a mixed powder of lactose and crystalline cellulose. Hydroxypropyl cellulose (HPC-SL (registered trademark), Nippon Soda Co., Ltd.) is described as a binder component.

WO 95/020380 discloses an orally disintegrating tablet which is highly disintegrating and is produced by spraying a sugar with high formability as a binding solution on a sugar with low formability.

The Japanese Pharmacopoeia, Fifteenth Edition and Japanese Pharmaceutical Excipients Directory 2016, edited by the Japan Pharmaceutical Excipients Council, Yakuji Nippo Ltd., Feb. 18, 2016 describe standards for lactose, maltitol and hydroxypropyl cellulose having a certain viscosity.

However, in WO 99/002158 disclosing a formulation containing nalfurafine hydrochloride, the content of the nalfurafine hydrochloride is 100 μg. Since the formulation disclosed in WO 99/002158 has a high content of the active ingredient, the active ingredient and the related substances are easily separated, which reduces the analysis interference derived from pharmaceutical additives. Thus, the formulation disclosed in WO 99/002158 does not have the problem of providing a highly pure tableted pharmaceutical composition.

WO 08/133330 describes a step of preparing a granulated product by spraying on mannitol a binder solution obtained by dissolving nalfurafine hydrochloride in water along with hydroxypropyl cellulose (HPC-SL (registered trademark) whose 2% aqueous solution has a viscosity of 3 to 5.9 mPa·s, Nippon Soda Co., Ltd.). However, there is no description of the granulation with hydroxypropyl cellulose whose 2% aqueous solution has a viscosity of greater than 5.9 mPa·s at 20° C., and there is no description about the analysis interference by related substances. Thus, it is not suggested that the use of a binder component such as hydroxypropyl cellulose having a specific viscosity will result in a highly pure tableted pharmaceutical composition.

WO 10/047381 discloses a step of preparing a granulated product by spraying on mannitol an aqueous solution of nalfurafine hydrochloride as a granulating solution, and describes that the resulting tablet disintegrates rapidly in an oral cavity. However, there is no description about the formability of the tablet and the effect of a specific binder component on the analysis interference.

WO 95/020380 discloses an orally disintegrating tablet which is highly disintegrating and is produced by spraying a sugar with high formability such as sorbitol, maltose, lactose, and fructose as a binding solution on a sugar with low formability such as mannitol, lactose, sucrose, glucose, and xylitol. However, since the active ingredient described in WO 95/020380 is different from nalfurafine, the effect of the related substances on the analysis interference is still unknown. Furthermore, the blending amount of the active ingredient is about 60 μg to about 21 mg. Thus, the content of the active ingredient is large, and the compatibility between good formability and high purity is not described.

On the other hand, The Japanese Pharmacopoeia, Fifteenth Edition and Japanese Pharmaceutical Excipients Directory 2016, edited by the Japan Pharmaceutical Excipients Council, Yakuji Nippo Ltd., Feb. 18, 2016 describe standards for lactose, maltitol and hydroxypropyl cellulose having a certain viscosity. According to the standards, the threshold values for impurities such as arsenic and heavy metals are specified, but a setting which is strict enough to be able to be applied to the quality control of tablets containing a very low content of nalfurafine or a pharmaceutically acceptable acid addition salt thereof is not provided.

It could therefore be helpful to provide a highly pure tableted pharmaceutical composition which comprises as an active ingredient nalfurafine or a pharmaceutically acceptable acid addition salt thereof, which has a handleable formability, and which facilitates the control of related substances.

SUMMARY

We found that, when producing a tablet such that 0.1 to 10 μg of nalfurafine or a pharmaceutically acceptable acid addition salt thereof is contained in the pharmaceutical composition, the control of the weight of a specific binder component allows for the compatibility between good formability and quality control of related substances.

We thus provide (1) to (7).
(1) A tableted pharmaceutical composition comprising nalfurafine or a pharmaceutically acceptable acid addition salt thereof; a binder component selected from the group consisting of maltose, maltitol, dextrin and pullulan; and a carrier, wherein the nalfurafine or a pharmaceutically acceptable acid addition salt thereof is contained in an amount of 0.1 to 10 μg, and the weight of the binder component is 100,000 to 2,000,000 weight % based on the weight of the nalfurafine or a pharmaceutically acceptable acid addition salt thereof and 5 to 20 weight % based on the total weight of the resulting pharmaceutical composition.
(2) A tableted pharmaceutical composition comprising nalfurafine or a pharmaceutically acceptable acid addition salt thereof; a binder component containing hydroxypropyl cellulose whose 2% aqueous solution has a viscosity of greater than 5.9 mPa·s at 20° C.; and a carrier, wherein the nalfurafine or a pharmaceutically acceptable acid addition salt thereof is contained in an amount of 0.1 to 10 μg, and the weight of the binder component is 20,000 to 500,000 weight % based on the weight of the nalfurafine or a pharmaceutically acceptable acid addition salt thereof and 1 to 5 weight % based on the total weight of the resulting pharmaceutical composition.
(3) The pharmaceutical composition according to (1), wherein the weight of the binder component is 100,000 to 400,000 weight % based on the weight of the nalfurafine or a pharmaceutically acceptable acid addition salt thereof.
(4) The pharmaceutical composition according to (2), wherein the weight of the binder component is 20,000 to 100,000 weight % based on the weight of the nalfurafine or a pharmaceutically acceptable acid addition salt thereof.
(5) The pharmaceutical composition according to any one of (1) to (4), wherein the nalfurafine or a pharmaceutically acceptable acid addition salt thereof is contained in an amount of 1 to 5 μg.
(6) The pharmaceutical composition according to any one of (1) to (5), wherein the carrier is selected from the group consisting of mannitol, glucose, anhydrous crystalline fructose, lactose and maltitol.
(7) A tablet composed of the pharmaceutical composition according to any one of (1) to (6).

A tableted pharmaceutical composition which contains nalfurafine or a pharmaceutically acceptable acid addition salt thereof and which is excellent in formability and quality control of related substances can be provided, and the utility and the safety as a pharmaceutical product can be enhanced.

DETAILED DESCRIPTION

Figure 1:
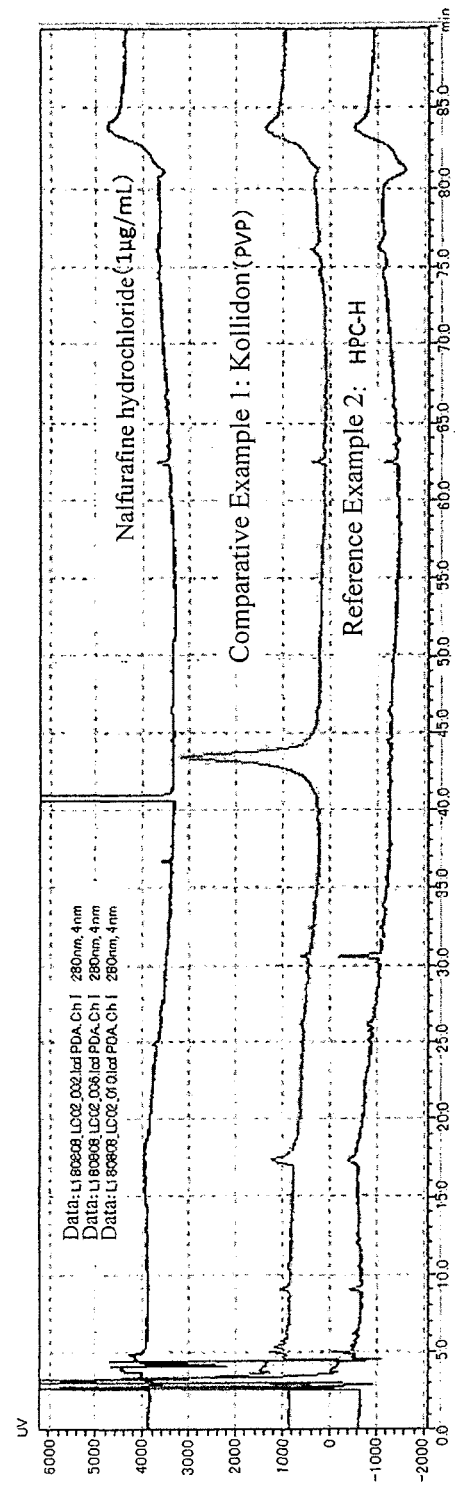
FIG. 1 shows the peak comparison among chromatograms of an aqueous solution of nalfurafine hydrochloride, Comparative Example 1 (PVP) and Reference Example 2 (HPC-H).

Examples will be described below. However, this disclosure is not limited to the following examples.

The tablet is a solid formulation formed by compression of powder and may be either an oral tablet or a parenteral tablet. Specific examples thereof include immediate release tablets, enteric coated tablets, sustained release tablets, orally disintegrating tablets and mini-tablets.

The active ingredient is nalfurafine or a pharmaceutically acceptable acid addition salt thereof. Examples of the pharmaceutically acceptable acid addition salts include mineral acid salts such as hydrochloric acid salt, sulfuric acid salt, nitric acid salt, hydrobromic acid salt, hydroiodic acid salt and phosphoric acid salt; organic carboxylic acid salts such as acetic acid salt, lactic acid salt, citric acid salt, oxalic acid salt, glutaric acid salt, malic acid salt, tartaric acid salt, fumaric acid salt, mandelic acid salt, maleic acid salt, benzoic acid salt and phthalic acid salt; and organic sulfonic acid salts such as methanesulfonic acid salt, ethanesulfonic acid salt, benzene sulfonic acid salt, p-toluene sulfonic acid salt and camphor sulfonic acid salt. Among them, hydrochloric acid salt, hydrobromic acid salt, phosphoric acid salt, tartaric acid salt, maleic acid salt, and methanesulfonic acid salt are preferred, and hydrochloric acid salt is the most preferred because of easy availability.

In the pharmaceutical composition, as long as it is tableted, the active ingredient, nalfurafine or a pharmaceutically acceptable acid addition salt thereof may be divided into tablets in any manner. The pharmaceutical composition includes those which contain all the nalfurafine or a pharmaceutically acceptable acid addition salt thereof in a single tablet or those which contain dividedly a required amount of nalfurafine or a pharmaceutically acceptable acid addition salt thereof in a plurality of tablets such as mini-tablets. In addition, the pharmaceutical composition is tableted such that 0.1 to 10 μg of nalfurafine or a pharmaceutically acceptable acid addition salt thereof is contained, and preferably tableted such that 1 to 5 μg is contained.

The binder components are maltitol, maltose, dextrin, pullulan and hydroxypropyl cellulose whose 2% aqueous solution has a viscosity of greater than 5.9 mPa·s at 20° C., all having a characteristic of adhering particles containing the active ingredient to each other when the active ingredient is made into powder or an aqueous solution, and any one commercially available may be used. These binder components differ in the optimal blending amount in the tableted pharmaceutical composition from the viewpoint of the adhesion or the control of related substances.

Hydroxypropyl cellulose has different solubility depending on the degree of polymerization. Therefore, hydroxypropyl cellulose having a higher degree of polymerization is less soluble in a solvent and thus fulfills better the function as a binder component. Therefore, hydroxypropyl cellulose has a high degree of polymerization, and exhibits a viscosity property of greater than 5.9 mPa·s in a 2% aqueous solution at 20° C. Examples of the hydroxypropyl cellulose whose 2% aqueous solution has a viscosity of greater than 5.9 mPa·s at 20° C. include HPC-L (manufactured by Nippon Soda Co., Ltd.), HPC-M (manufactured by Nippon Soda Co., Ltd.), and HPC-H (manufactured by Nippon Soda Co., Ltd.).

The blending amount of the binder component in the pharmaceutical composition is, when the binder component is selected from the group consisting of maltose, maltitol, dextrin and pullulan, 100,000 to 2,000,000 weight %, preferably 100,000 to 400,000 weight %, based on the weight of nalfurafine or a pharmaceutically acceptable acid addition salt thereof, and 5 to 20 weight % based on the total weight of the pharmaceutical composition. In less than 100,000 weight % based on the weight of nalfurafine or a pharmaceutically acceptable acid addition salt thereof or less than 5 weight % based on the total weight of the pharmaceutical composition, the formability is insufficient. On the other hand, when the blending amount of the binder component exceeds 2,000,000 weight % based on the weight of nalfurafine or a pharmaceutically acceptable acid addition salt thereof or exceeds 20 weight % based on the total weight of the pharmaceutical composition, the control of related substances becomes difficult because many analysis peaks derived from the binder component are detected.

The blending amount of the binder component in the pharmaceutical composition is, in hydroxypropyl cellulose whose 2% aqueous solution has a viscosity of greater than 5.9 mPa·s at 20° C., 20,000 to 500,000 weight %, preferably 20,000 to 100,000 weight %, based on the weight of nalfurafine or a pharmaceutically acceptable acid addition salt thereof, and 1 to 5 weight % based on the total weight of the pharmaceutical composition. In less than 20,000 weight % based on the weight of nalfurafine or a pharmaceutically acceptable acid addition salt thereof or less than 1 weight % based on the total weight of the pharmaceutical composition, the formability is insufficient. On the other hand, when the blending amount of the binder component exceeds 500,000 weight % based on the weight of nalfurafine or a pharmaceutically acceptable acid addition salt thereof or exceeds 5 weight % based on the total weight of the pharmaceutical composition, the control of related substances becomes difficult because many analysis peaks derived from the binder component are detected.

The carrier is an additive that dilutes the active ingredient so that the tablet can have a size easy to administer, and any pharmaceutical additive with a high purity can be used without limitation. Among carriers, mannitol, glucose, anhydrous crystalline fructose, lactose, and maltitol are preferred because of the high purity in the analysis of nalfurafine or a pharmaceutically acceptable acid addition salt thereof and related substances thereof.

The tableted pharmaceutical composition means that, when the tablet is analyzed by an analysis method using high performance chromatography (hereinafter also referred to as HPLC) which will be described below, except the peaks corresponding to nalfurafine or a pharmaceutically acceptable acid addition salt thereof and related substances thereof, the component amount of impurities of 1% or more, more preferably, 0.1% or more, based on the active ingredient, is not recognized during the retention time of 20 to 75 minutes of nalfurafine or a pharmaceutically acceptable acid addition salt thereof and related substances thereof. The criteria for these impurities are established from the threshold values of impurity safety confirmation and reports defined by the ICH (ICH-Q3 Guideline for Impurities in New Drug Products).

HPLC Conditions

Sample preparation: water is added to a pharmaceutical composition to attain a concentration of nalfurafine or a pharmaceutically acceptable acid addition salt thereof of 1 μg/mL at the time of the measurement, and the extraction is carried out under appropriate stirring. The extract is centrifuged, and the supernatant is used as a measurement sample.

Standard solution preparation: nalfurafine or a pharmaceutically acceptable acid addition salt thereof is added to water and thus dissolved in water to attain a concentration of 1 μg/mL, and used as a measurement sample.

Detector: ultraviolet absorptiometer (measurement wavelength: 280 nm)

Column: stainless steel tube having an inner diameter of 4.6 mm and a length of 250 mm packed with octadecylsilylated silica gel of 5 μm.

Mobile phase solution A: 50 mM aqueous solution of sodium dihydrogen phosphate/acetonitrile=95/5 (v/v)

Mobile phase solution B: 50 mM aqueous solution of sodium dihydrogen phosphate/acetonitrile=60/40 (v/v)

Column temperature: constant temperature around 40° C.

Flow rate: 1.0 mL/min

Analysis time: 20 minutes to 75 minutes

Concentration gradient:

HPLC Gradient Conditions

TABLE 1

| Time after injection (minutes) | Mobile phase A (volume %) | Mobile phase B (volume %) |
| --- | --- | --- |
| 0 to 10 | 100 | 0 |
| 10 to 75 | 100 → 0 | 0 → 100 |

Table 1 shows the variation in volume % (gradient conditions) of mobile phases A and B over time under HPLC conditions.

The component amount of impurities in Reference Examples, Comparative Examples, and Examples was calculated from the obtained HPLC peaks using the following formulas (1) and (2), and the impurity showing the largest component amount was determined.

The component amount of impurities in Reference Examples 1 to 10 and Comparative Examples 1 to 10(%)=(area value of the HPLC peak of each component in the sample/area value of the HPLC peak of nalfurafine or a pharmaceutically acceptable acid addition salt thereof in the standard solution)×100%  (1)

The component amount of impurities in Examples 1 to 5 and Comparative Example 11(%)=(area value of the HPLC peak of each component in the sample/the total area value of the HPLC peaks within the analysis time)×100%  (2)

In addition to the above-mentioned components, it is possible to add as necessary various additives used for the production of general formulations to the tableted pharmaceutical composition within the range that does not impair the desired effects. Such additives include, for example, excipients, disintegrants, lubricants, coating agents, fluidizing agents, flavoring agents, flavors, coloring agents and sweetening agents.

Examples of the disintegrants include crospovidone, croscarmellose sodium, carmellose calcium, sodium carboxymethyl starch, low-substituted hydroxypropyl cellulose and the like.

Examples of the lubricants include magnesium stearate, calcium stearate, sodium stearyl fumarate, talc, sucrose fatty acid esters, stearic acid, aluminum stearate, sodium potassium tartrate, light anhydrous silicic acid, carnauba wax, carmellose calcium, carmellose sodium, hydrated silicon dioxide, hydrogenated oils, hydrogenated rapeseed oils and the like.

Examples of the coating agents include hydroxypropyl methylcellulose, ethyl cellulose, sodium carboxymethyl ethyl cellulose, polyvinyl alcohol and the like.

Examples of the fluidizing agents include talc, hydrated silicon dioxide, light anhydrous silicic acid and the like.

Examples of the flavoring agents include glutamic acid, fumaric acid, succinic acid, citric acid, sodium citrate, tartaric acid, malic acid, ascorbic acid, sodium chloride, menthol and the like.

Examples of the flavors include orange, vanilla, strawberry and yogurt flavors, menthol and the like.

Examples of the coloring agents include titanium oxide, red ferric oxide, yellow ferric oxide, black iron oxide, talc, edible pigments such as Red No. 3, Yellow No. 5, and Blue No. 1, riboflavin and the like.

Examples of the sweetening agents include aspartame, saccharin, dipotassium glycyrrhizinate, stevia and the like.

The method of producing the tableted pharmaceutical composition can be carried out by a wet granulation step or a dry granulation step or a dry mixing step followed by the compression forming.

In the wet granulation process, there is no limitation on the method of adding a binder component as a liquid or suspension. Examples thereof include a method in which a granulated product is obtained by dissolving or suspending the binder component in water or a pharmaceutically acceptable solvent and the resulting liquid (solution or suspension) is added to a carrier. In this example, the active ingredient may be dissolved in a solution of the binder component to produce a granulated product, or the active ingredient may be mixed with the granulated product.

In addition, in the wet granulation process, there is no limitation on the method of adding a binder component as a solid. Examples thereof include a method in which a granulated product is obtained by mixing the binder component and a carrier and a pharmaceutically acceptable solvent is sprayed on this mixture. In this example, the active ingredient may be sprayed as a solution with the solvent, or the active ingredient may be mixed with the granulated product.

The wet granulation step is carried out using a commonly used apparatus, and examples thereof include fluidized bed granulators, tumbling fluidized bed granulators, stirring granulators, cylindrical extrusion granulators, wet extrusion granulators and the like. When water is used, for example, as a solvent for dissolving or suspending the active ingredient, a fluidized bed granulator, a tumbling fluidized bed granulator or a stirring granulator is suitable.

In the dry granulation process, there is no limitation on the method of adding a binder component. Examples thereof include a method in which a mixture of the active ingredient, the binder component and the carrier mixed in a mixer, or a dry mixture is compressed into flakes and then the flakes are ground into a suitable size.

The dry granulation step is carried out using a commonly used apparatus, and examples thereof include slugging process or roller compactor process.

Examples of the dry mixing step include a method of in which the active ingredient, the binder component and the carrier are mixed, followed by the compression forming of the mixture.

Moreover, light stability in a solid formulation can be further improved by incorporating yellow ferric oxide, red ferric oxide or black iron oxide as a coloring agent in the pharmaceutical composition. There is no limitation on the method of adding the coloring agent, but the coloring agent can be added by suspending the coloring agent in powder or water or a pharmaceutically acceptable solvent, and adding the resulting suspension.

A commonly used apparatus is used for compression forming, and examples thereof include a single punch tableting machine, a rotary tableting machine and the like. The forming pressure for tableting is not particularly limited as long as the tablet has hardness that does not cause any problem in handling.

The tableted pharmaceutical composition has certain formability that suppresses the exposure to medical workers caused by the production of powdery dust or that suppresses the contamination in a single package with other agents due to the powdery dust. The hardness of such a tablet may be, for example, 40 N or more when the diameter is 6 mm φ or more, and more preferably 50 N or more. As another example, when the diameter is less than 6 mm φ, the hardness of such a tablet may be 20 N or more, and more preferably 30 N or more.

EXAMPLES

To clarify the excellent effects of our compositions, this description includes Comparative Examples, Reference Examples and Examples, but this disclosure is not limited thereto. In Reference Examples and Comparative Examples, the experiments were performed without the addition of the active ingredient to clearly distinguish the peak derived from nalfurafine or a pharmaceutically acceptable acid addition salt thereof from the peaks derived from components other than the active ingredient such as the binder component.

Comparative Example 1

Assuming a tablet containing an amount equivalent to 1 µg of the active ingredient which is nalfurafine or a pharmaceutically acceptable acid addition salt thereof per 100 mg, 985 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 10 mg of polyvinyl pyrrolidone (PVP) (KOLLIDON (registered trademark) 30, manufactured by BASF Corporation) was dissolved in 200 µL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 µg/mL, and the maximum component amount of impurities was calculated.

Comparative Example 2

An experiment was conducted in the same manner as in Comparative Example 1 except that PVP in Comparative Example 1 was replaced with hydroxypropyl methylcellulose (HPMC 2910, manufactured by Shin-Etsu Chemical Co., Ltd.). Specifically, assuming a tablet containing an amount equivalent to 1 μg of the active ingredient which is nalfurafine or a pharmaceutically acceptable acid addition salt thereof per 100 mg, 985 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 10 mg of hydroxypropyl methylcellulose (HPMC 2910, manufactured by Shin-Etsu Chemical Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Comparative Example 3

An experiment was conducted in the same manner as in Comparative Example 1 except that PVP in Comparative Example 1 was replaced with hydroxypropyl cellulose whose 2% aqueous solution has a viscosity of 3 to 5.9 mPa·s at 20° C. (HPC-SL, manufactured by Nippon Soda Co., Ltd.). Specifically, assuming a tablet containing an amount equivalent to 1 μg of the active ingredient which is nalfurafine or a pharmaceutically acceptable acid addition salt thereof per 100 mg, 985 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 10 mg of hydroxypropyl cellulose whose 2% aqueous solution has a viscosity of 3 to 5.9 mPa·s at 20° C. (HPC-SL, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 1

An experiment was conducted in the same manner as in Comparative Example 1 except that PVP in Comparative Example 1 was replaced with hydroxypropyl cellulose whose 2% aqueous solution has a viscosity of 6 to 10 mPa·s at 20° C. (HPC-L, manufactured by Nippon Soda Co., Ltd.). Specifically, assuming a tablet containing an amount equivalent to 1 μg of the active ingredient which is nalfurafine or a pharmaceutically acceptable acid addition salt thereof per 100 mg, 985 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 10 mg of hydroxypropyl cellulose whose 2% aqueous solution has a viscosity of 6 to 10 mPa·s at 20° C. (HPC-L, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 2

An experiment was conducted in the same manner as in Comparative Example 1 except that PVP in Comparative Example 1 was replaced with hydroxypropyl cellulose whose 2% aqueous solution has a viscosity of 1000 to 4000 mPa·s at 20° C. (HPC-H, manufactured by Nippon Soda Co., Ltd.). Specifically, assuming a tablet containing an amount equivalent to 1 μg of the active ingredient which is nalfurafine or a pharmaceutically acceptable acid addition salt thereof per 100 mg, 985 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 10 mg of hydroxypropyl cellulose whose 2% aqueous solution has a viscosity of 1000 to 4000 mPa·s at 20° C. (HPC-H, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Effects of Various Polymers as Binder Components

TABLE 2

| | Comparative Example 1 | Comparative Example 2 | Comparative Example 3 | Reference Example 1 | Reference Example 2 |
|---|---|---|---|---|---|
| Blending amount of active ingredient | The content of 1 to 5 μg of the active ingredient in 100 mg of the tableted pharmaceutical composition is assumed | | | | |
| Binder component/active ingredient (weight %) | 20,000% to 100,000% | 20,000% to 100,000% | 20,000% to 100,000% | 20,000% to 100,000% | 20,000% to 100,000% |
| Binder component/pharmaceutical composition (weight %) | 1% | 1% | 1% | 1% | 1% |

TABLE 2-continued

|  |  | Comparative Example 1 | Comparative Example 2 | Comparative Example 3 | Reference Example 1 | Reference Example 2 |
|---|---|---|---|---|---|---|
| Binder component | Type | PVP (Kollidon 30) | HPMC2910 | HPC-SL | HPC-L | HPC-H |
|  | Blending ratio | 1% | 1% | 1% | 1% | 1% |
| Carrier | Type | Mannitol | Mannitol | Mannitol | Mannitol | Mannitol |
|  | Blending ratio | 98.5% | 98.5% | 98.5% | 98.5% | 98.5% |
| Formability |  | ◎ (65N) | X (35N) | ○ (49N) | ○ (44N) | ◎ (60N) |
| High purity |  | X (18.9%) | X (5.16%) | X (1.07%) | ◎ (0.00%) | ○ (0.65%) |

Amount of the active ingredient: The dose of the active ingredient per day is assumed to be 1 μg
Formability criteria: ○ in the case of 40N or more and ◎ in the case of 50N or more.
High purity criteria: In the tableted pharmaceutical composition containing 1 μg of the active ingredient, X in the case of more than 1%, ○ in the case of 1% or less, and ◎ in the case of 0.1% or less.

Table 2 shows the effect of a variety of different polymers as binder components in Comparative Examples 1 to 3 and Reference Examples 1 and 2 on the formability of the tablet and on the purity of the tableted pharmaceutical composition. As shown in Table 2, in Reference Examples 1 and 2 in which hydroxypropyl cellulose whose 2% aqueous solution has a viscosity of greater than 5.9 mPa·s at 20° C. was added, the tablets showed high formability and the peak corresponding to the component amount of impurities of 1% or more based on the active ingredient was not recognized during the retention time of 20 to 75 minutes. Thus, we confirmed that a highly pure tableted pharmaceutical composition was obtained.

Comparative Example 4

An experiment was conducted in the same manner as in Reference Example 1 except that the blending amount of mannitol in Reference Example 1 was changed to 895 mg and the blending amount of hydroxypropyl cellulose (HPC-L, manufactured by Nippon Soda Co., Ltd.) was changed to 100 mg. Specifically, assuming a tablet containing an amount equivalent to 1 μg of the active ingredient which is nalfurafine or a pharmaceutically acceptable acid addition salt thereof per 100 mg, 895 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 100 mg of hydroxypropyl cellulose whose 2% aqueous solution has a viscosity of 6 to 10 mPa·s at 20° C. (HPC-L, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 3

An experiment was conducted in the same manner as in Reference Example 1 except that the blending amount of mannitol in Reference Example 1 was changed to 945 mg and the blending amount of hydroxypropyl cellulose (HPC-L, manufactured by Nippon Soda Co., Ltd.) was changed to 50 mg. Specifically, assuming a tablet containing an amount equivalent to 1 μg of the active ingredient which is nalfurafine or a pharmaceutically acceptable acid addition salt thereof per 100 mg, 945 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 50 mg of hydroxypropyl cellulose whose 2% aqueous solution has a viscosity of 6 to 10 mPa·s at 20° C. (HPC-L, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 4

An experiment was conducted in the same manner as in Reference Example 1 except that the blending amount of mannitol in Reference Example 1 was changed to 955 mg and the blending amount of hydroxypropyl cellulose (HPC-L, manufactured by Nippon Soda Co., Ltd.) was changed to 40 mg. Specifically, assuming a tablet containing an amount equivalent to 1 μg of the active ingredient which is nalfurafine or a pharmaceutically acceptable acid addition salt thereof per 100 mg, 945 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 50 mg of hydroxypropyl cellulose whose 2% aqueous solution has a viscosity of 6 to 10 mPa·s at 20° C. (HPC-L, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 5

An experiment was conducted in the same manner as in Reference Example 1 except that the blending amount of mannitol in Reference Example 1 was changed to 965 mg and the blending amount of hydroxypropyl cellulose (HPC-L, manufactured by Nippon Soda Co., Ltd.) was changed to 30 mg. Specifically, assuming a tablet containing an amount equivalent to 1 μg of the active ingredient which is nalfurafine or a pharmaceutically acceptable acid addition salt thereof per 100 mg, 965 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 30 mg of hydroxypropyl cellulose whose 2% aqueous solution has a viscosity of 6 to 10 mPa·s at 20° C. (HPC-L, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 6

An experiment was conducted in the same manner as in Reference Example 1 except that the blending amount of mannitol in Reference Example 1 was changed to 975 mg and the blending amount of hydroxypropyl cellulose (HPC-L, manufactured by Nippon Soda Co., Ltd.) was changed to 20 mg. Specifically, assuming a tablet containing an amount equivalent to 1 μg of the active ingredient which is nalfurafine or a pharmaceutically acceptable acid addition salt thereof per 100 mg, 975 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 20 mg of hydroxypropyl cellulose whose 2% aqueous solution has a viscosity of 6 to 10 mPa·s at 20° C. (HPC-L, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 7

An experiment was conducted in the same manner as in Reference Example 1 except that the blending amount of mannitol in Reference Example 1 was changed to 985 mg and the blending amount of hydroxypropyl cellulose (HPC-L, manufactured by Nippon Soda Co., Ltd.) was changed to 10 mg. Specifically, assuming a tablet containing an amount equivalent to 1 μg of the active ingredient which is nalfurafine or a pharmaceutically acceptable acid addition salt thereof per 100 mg, 985 mg of mannitol (PEARLITOL (registered trademark) 50C, manufactured by Roquette Japan K.K.) and 10 mg of magnesium stearate (Taihei Chemical Industrial Co., Ltd.) were mixed in a bag to obtain a mixture sample. Then, 20 mg of hydroxypropyl cellulose whose 2% aqueous solution has a viscosity of 6 to 10 mPa·s at 20° C. (HPC-L, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Comparative Example 5

An experiment was conducted in the same manner as in Reference Example 1 except that the blending amount of mannitol in Reference Example 1 was changed to 990 mg and the blending amount of hydroxypropyl cellulose (HPC-L, manufactured by Nippon Soda Co., Ltd.) was changed to 5 mg. Specifically, assuming a tablet containing an amount equivalent to 1 μg of the active ingredient which is nalfurafine or a pharmaceutically acceptable acid addition salt thereof per 100 mg, 990 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 20 mg of hydroxypropyl cellulose whose 2% aqueous solution has a viscosity of 6 to 10 mPa·s at 20° C. (HPC-L, manufactured by Nippon Soda Co., Ltd.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ. The hardness of this tablet was measured with a hardness meter (manufactured by Okada Seiko Co., Ltd., PC-30). The extract extracted from 0.5 g of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Desired Range of the Amount of Addition When Hydroxypropyl Cellulose Whose 2% Aqueous Solution has a Viscosity of Greater than 5.9 mPa·s at 20° C. is Used as a Binder

TABLE 3

|  | Comparative Example 4 | Reference Example 3 | Reference Example 4 | Reference Example 5 | Reference Example 6 | Reference Example 7 | Comparative Example 5 |
|---|---|---|---|---|---|---|---|
| Blending amount of active ingredient | The content of 1 to 5 μg of the active ingredient in 100 mg of the tableted pharmaceutical composition is assumed | | | | | | |
| Binder component/active ingredient (weight %) | 200,000% to 1,000,000% | 100,000% to 500,000% | 80,000% to 400,000% | 60,000% to 300,000% | 40,000% to 200,000% | 20,000% to 100,000% | 10,000% to 50,000% |

TABLE 3-continued

|  |  | Comparative Example 4 | Reference Example 3 | Reference Example 4 | Reference Example 5 | Reference Example 6 | Reference Example 7 | Comparative Example 5 |
|---|---|---|---|---|---|---|---|---|
| Binder component/pharmaceutical composition (weight %) |  | 10% | 5% | 4% | 3% | 2% | 1% | 0.5% |
| Binder | Type |  |  |  | HPC-L |  |  |  |
| component | Blending ratio | 10% | 5% | 4% | 3% | 2% | 1% | 0.5% |
| Carrier | Type | Mannitol | Mannitol | Mannitol | Mannitol | Mannitol | Mannitol | Mannitol |
|  | Blending ratio | 89.5% | 94.5% | 95.5% | 96.5% | 97.5% | 98.5% | 99.0% |
| Formability |  | ◎ (59N) | ◎ (57N) | ◎ (59N) | ◎ (54N) | ○ (46N) | ○ (44N) | X (38N) |
| High purity |  | X (4.3%) | ○ (0.63%) | ○ (0.57%) | ○ (0.45%) | ◎ (0.00%) | ◎ (0.00%) | ◎ (0.00%) |

Amount of the active ingredient: The dose of the active ingredient per day is assumed to be 1 μg
Formability criteria: ○ in the case of 40N or more and ◎ in the case of 50N or more.
High purity criteria: In the tableted pharmaceutical composition containing 1 μg of the active ingredient, X in the case of more than 1%, ○ in the case of 1% or less, and ◎ in the case of 0.1% or less.

Table 3 shows the effect of the changes of the weight ratio of the binder component to the active ingredient and the blending ratio of the binder component in the pharmaceutical composition in Comparative Examples 4 and 5 and Reference Examples 3 to 7 on the formability of the tablet and on the purity of the tableted pharmaceutical composition. As shown in Table 3, for the blending ratio of hydroxypropyl cellulose whose 2% aqueous solution has a viscosity of greater than 5.9 mPa·s at 20° C. to the pharmaceutical composition in Reference Examples 3 to 7, the range of 1 to 5 weight % resulted in the compatibility between formability and high purity.

Peak Comparison Among Chromatograms

As shown in FIG. 1, the tablets of Reference Example 2 and Comparative Example 1 were analyzed by the analysis method using high performance chromatography to compare their chromatograms. In Reference Example 2, no peak corresponding to the component amount of impurities of 1% or more based on the active ingredient was recognized within 20 to 75 minutes. Thus, we confirmed that a highly pure tableted pharmaceutical composition was obtained.

Comparative Example 6

Assuming a tablet containing an amount equivalent to 1 μg of the active ingredient which is nalfurafine or a pharmaceutically acceptable acid addition salt thereof per 100 mg, 945 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 50 mg of sorbitol (manufactured by Roquette Japan K.K.) was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ (the expected content of the active ingredient of 1 μg/tablet). The hardness of this tablet was measured with a hardness meter (manufactured by Okada Seiko Co., Ltd., PC-30). The extract extracted from 0.5 g (the expected content of the active ingredient of 5 μg) of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Comparative Example 7

An experiment was conducted in the same manner as in Comparative Example 6 except that sorbitol in Comparative Example 6 was replaced with lactose (lactose monohydrate, manufactured by DMV-Fonterra Excipients). Specifically, assuming a tablet containing an amount equivalent to 1 μg of the active ingredient which is nalfurafine or a pharmaceutically acceptable acid addition salt thereof per 100 mg, 945 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 50 mg of lactose was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ (the expected content of the active ingredient of 1 μg/tablet). The hardness of this tablet was measured with a hardness meter (manufactured by Okada Seiko Co., Ltd., PC-30). The extract extracted from 0.5 g (the expected content of the active ingredient of 5 μg) of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Comparative Example 8

An experiment was conducted in the same manner as in Comparative Example 6 except that sorbitol in Comparative Example 6 was replaced with anhydrous crystalline fructose (manufactured by Danisco Japan Ltd.). Specifically, assuming a tablet containing an amount equivalent to 1 μg of the active ingredient which is nalfurafine or a pharmaceutically acceptable acid addition salt thereof per 100 mg, 945 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 50 mg of anhydrous crystalline fructose was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ (the expected content of the active ingredient of 1 μg/tablet). The hardness of this tablet was measured with a hardness meter (manufactured by Okada Seiko Co., Ltd., PC-30). The extract extracted from 0.5 g (the expected content of the active ingredient of 5 μg) of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Comparative Example 9

An experiment was conducted in the same manner as in Comparative Example 6 except that sorbitol in Comparative Example 6 was replaced with maltose (manufactured by Hayashibara Co., Ltd.). Specifically, assuming a tablet containing an amount equivalent to 1 μg of the active ingredient which is nalfurafine or a pharmaceutically acceptable acid addition salt thereof per 100 mg, 945 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 50 mg of maltose was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ (the expected content of the active ingredient of 1 μg/tablet). The hardness of this tablet was measured with a hardness meter (manufactured by Okada Seiko Co., Ltd., PC-30). The extract extracted from 0.5 g (the expected content of the active ingredient of 5 μg) of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 8

An experiment was conducted in the same manner as in Comparative Example 6 except that sorbitol in Comparative Example 6 was replaced with pullulan (manufactured by Hayashibara Co., Ltd.). Specifically, assuming a tablet containing an amount equivalent to 1 μg of the active ingredient which is nalfurafine or a pharmaceutically acceptable acid addition salt thereof per 100 mg, 945 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 50 mg of pullulan was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ (the expected content of the active ingredient of 1 μg/tablet). The hardness of this tablet was measured with a hardness meter (manufactured by Okada Seiko Co., Ltd., PC-30). The extract extracted from 0.5 g (the expected content of the active ingredient of 5 μg) of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 9

An experiment was conducted in the same manner as in Comparative Example 6 except that sorbitol in Comparative Example 6 was replaced with dextrin (manufactured by Nippon Starch Chemical Co., Ltd.). Specifically, assuming a tablet containing an amount equivalent to 1 μg of the active ingredient which is nalfurafine or a pharmaceutically acceptable acid addition salt thereof per 100 mg, 945 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 50 mg of dextrin was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ (the expected content of the active ingredient of 1 μg/tablet). The hardness of this tablet was measured with a hardness meter (manufactured by Okada Seiko Co., Ltd., PC-30). The extract extracted from 0.5 g (the expected content of the active ingredient of 5 μg) of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Reference Example 10

An experiment was conducted in the same manner as in Comparative Example 6 except that sorbitol in Comparative Example 6 was replaced with mannitol (manufactured by Roquette Japan K.K.). Specifically, assuming a tablet containing an amount equivalent to 1 μg of the active ingredient which is nalfurafine or a pharmaceutically acceptable acid addition salt thereof per 100 mg, 945 mg of mannitol (PEARLITOL (registered trademark) 50C, manufactured by Roquette Japan K.K.) and 5 mg of magnesium stearate (Taihei Chemical Industrial Co., Ltd.) were mixed in a bag to obtain a mixture sample. Then, 50 mg of mannitol was dissolved in 200 μL of water to form a solution of a binder component, and this solution was added to the mixture sample and granules were formed in a mortar, to prepare a granulated product. A hydraulic press was used at 100 kgf to pressurize 100 mg of this granulated product to prepare a tablet (1 tablet) of 6 mm φ (the expected content of the active ingredient of 1 μg/tablet). The hardness of this tablet was measured with a hardness meter (manufactured by Okada Seiko Co., Ltd., PC-30). The extract extracted from 0.5 g (the expected content of the active ingredient of 5 μg) of this granulated product with 5 mL of water was analyzed by HPLC, and the area values of the obtained peaks were compared to the area value corresponding to nalfurafine hydrochloride of 1 μg/mL, and the maximum component amount of impurities was calculated.

Effects of Various Sugars as Binder Components

TABLE 4

|  | Comparative Example 6 | Comparative Example 7 | Comparative Example 8 | Comparative Example 9 | Reference Example 8 | Reference Example 9 | Reference Example 10 |
|---|---|---|---|---|---|---|---|
| Blending amount of active ingredient | The content of 1 to 5 μg of the active ingredient in 100 mg of the tableted pharmaceutical composition is assumed | | | | | | |
| Binder component/active ingredient (weight %) | 100,000% to 500,000% | 100,000% to 500,000% | 100,000% to 500,000% | 100,000% to 500,000% | 100,000% to 500,000% | 100,000% to 500,000% | 100,000% to 500,000% |
| Binder component/pharmaceutical composition (weight %) | 5% | 5% | 5% | 5% | 5% | 5% | 5% |

TABLE 4-continued

|  |  | Comparative Example 6 | Comparative Example 7 | Comparative Example 8 | Comparative Example 9 | Reference Example 8 | Reference Example 9 | Reference Example 10 |
|---|---|---|---|---|---|---|---|---|
| Binder component | Type | Sorbitol | Lactose | Anhydrous crystalline fructose | Maltose | Pullulan | Dextrin | Mannitol |
|  | Blending ratio | 5% | 5% | 5% | 5% | 5% | 5% | 5% |
| Carrier | Type | Mannitol | Mannitol | Mannitol | Mannitol | Mannitol | Mannitol | Mannitol |
|  | Blending ratio | 94.5% | 94.5% | 94.5% | 94.5% | 94.5% | 94.5% | 94.5% |
| Formability |  | X (10N) | X (39N) | X (9N) | X (17N) | ◎ (84N) | ◎ (85N) | ◎ (58N) |
| High purity |  | ○ (0.81%) | ○ (0.36%) | ○ (0.42%) | ○ (0.38%) | ◎ (0.00%) | ○ (0.59%) | ○ (0.48%) |

Amount of the active ingredient: The dose of the active ingredient per day is assumed to be 1 μg
Formability criteria: ○ in the case of 40N or more and ◎ in the case of 50N or more.
High purity criteria: In the tableted pharmaceutical composition containing 1 μg of the active ingredient, x in the case of more than 1%, ○ in the case of 1% or less, and ◎ in the case of 0.1% or less.

Table 4 shows the effect of different binder components in Comparative Examples 6 to 9 and Reference Examples 8 to 10 on the formability of the tablet and on the purity of the tableted pharmaceutical composition. As shown in Table 4, compared to Comparative Examples 6 to 9, pullulan, dextrin, mannitol and HPC-L of Reference Examples 8 to 10 resulted in the compatibility between formability and high purity.

Reference Example 11

Assuming that the expected amount to be added of nalfurafine or a pharmaceutically acceptable acid addition salt thereof was 10 μg, 1 g of mannitol was placed in a centrifuge tube and 10 mL of distilled water was added and stirred, and the obtained supernatant was used as Reference Example 11. Reference Example 11 was analyzed by HPLC, and the area values of the obtained peaks were compared to the area value corresponding to nalfurafine hydrochloride of 1 μg/mL, and the maximum component amount of impurities was calculated. As shown in Table 5, the maximum component amount of the impurities in Reference Example 11 was 0.00%.

Reference Example 12

Reference Example 12 was prepared in the same manner except that mannitol in Reference Example 11 was replaced with glucose (manufactured by San-Ei Gen F.F.I., Inc.). Specifically, assuming that the expected amount to be added of nalfurafine or a pharmaceutically acceptable acid addition salt thereof was 10 μg, 1 g of glucose (manufactured by San-Ei Gen F.F.I., Inc.) was placed in a centrifuge tube and 10 mL of distilled water was added and stirred, and the obtained supernatant was used as Reference Example 12. An experiment was conducted in the same manner as in Reference Example 11, and the area values of the obtained peaks were compared to the area value corresponding to nalfurafine hydrochloride of 1 μg/mL, and the maximum component amount of impurities was calculated. As shown in Table 5, the maximum component amount of the impurities in Reference Example 12 was 0.00%.

Reference Example 13

Reference Example 13 was prepared in the same manner except that mannitol in Reference Example 11 was replaced with anhydrous crystalline fructose (manufactured by Danisco Japan Ltd.). Specifically, assuming that the expected amount to be added of nalfurafine or a pharmaceutically acceptable acid addition salt thereof was 10 μg, 1 g of anhydrous crystalline fructose (manufactured by Danisco Japan Ltd.) was placed in a centrifuge tube and 10 mL of distilled water was added and stirred, and the obtained supernatant was used as Reference Example 13. An experiment was conducted in the same manner as in Reference Example 11, and the area values of the obtained peaks were compared to the area value corresponding to nalfurafine hydrochloride of 1 μg/mL, and the maximum component amount of impurities was calculated. As shown in Table 5, the maximum component amount of the impurities in Reference Example 13 was 0.00%.

Reference Example 14

Reference Example 14 was prepared in the same manner except that mannitol in Reference Example 11 was replaced with lactose (lactose monohydrate, manufactured by DMV-Fonterra Excipients). Specifically, assuming that the expected amount to be added of nalfurafine or a pharmaceutically acceptable acid addition salt thereof was 10 μg, 1 g of lactose (lactose monohydrate, manufactured by DMV-Fonterra Excipients) was placed in a centrifuge tube and 10 mL of distilled water was added and stirred, and the obtained supernatant was used as Reference Example 14. An experiment was conducted in the same manner as in Reference Example 11, and the area values of the obtained peaks were compared to the area value corresponding to nalfurafine hydrochloride of 1 μg/mL, and the maximum component amount of impurities was calculated. As shown in Table 5, the maximum component amount of the impurities in Reference Example 14 was 0.35%.

Reference Example 15

Reference Example 15 was prepared in the same manner except that mannitol in Reference Example 11 was replaced with maltitol (manufactured by Hayashibara Co., Ltd.). Specifically, assuming that the expected amount to be added of nalfurafine or a pharmaceutically acceptable acid addition salt thereof was 10 μg, 1 g of maltitol (manufactured by Hayashibara Co., Ltd.) was placed in a centrifuge tube and 10 mL of distilled water was added and stirred, and the obtained supernatant was used as Reference Example 15. An experiment was conducted in the same manner as in Reference Example 11, and the area values of the obtained peaks were compared to the area value corresponding to nalfurafine hydrochloride of 1 μg/mL, and the maximum component amount of impurities was calculated. As shown in Table 5, the maximum component amount of the impurities in Reference Example 15 was 0.32%.

Comparative Example 10

Comparative Example 10 was prepared in the same manner except that mannitol in Reference Example 11 was replaced with sucrose (manufactured by Suzu Pharmaceutical Co., Ltd.). Specifically, assuming that the expected amount to be added of nalfurafine or a pharmaceutically acceptable acid addition salt thereof was 10 μg, 1 g of sucrose (manufactured by Suzu Pharmaceutical Co., Ltd.) was placed in a centrifuge tube and 10 mL of distilled water was added and stirred, and the obtained supernatant was used as Comparative Example 10. An experiment was conducted in the same manner as in Reference Example 11, and the area values of the obtained peaks were compared to the area value corresponding to nalfurafine hydrochloride of 1 μg/mL, and the maximum component amount of impurities was calculated. As shown in Table 5, the maximum component amount of the impurities in Comparative Example 10 was 1.28%.

Purity of Various Sugars as Carriers

TABLE 5

|  | Reference Example 11 | Reference Example 12 | Reference Example 13 | Reference Example 14 | Reference Example 15 | Comparative Example 10 |
|---|---|---|---|---|---|---|
| Carrier Type | Mannitol | Glucose | Anhydrous crystalline fructose | Lactose | Maltitol | Sucrose |
| High purity | ◎ (0.00%) | ◎ (0.00%) | ◎ (0.00%) | ○ (0.35%) | ○ (0.32%) | X (1.28%) |

High purity criteria: In the tableted pharmaceutical composition containing 1 μg of the active ingredient, X in the case of more than 1%, ○ in the case of 1% or less, and ◎ in the case of 0.1% or less.

Table 5 shows the effect of different carriers in Reference Examples 11 to 15 and Comparative Example 10 on the purity of the tableted pharmaceutical composition.

Chromatogram Comparison

Figure 2:
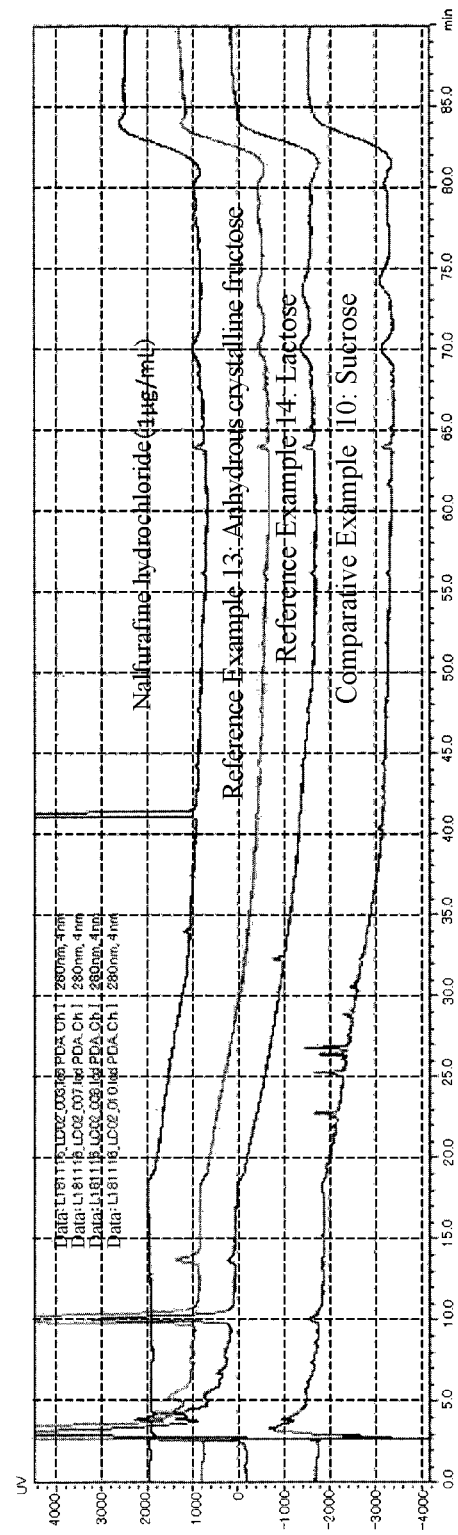
FIG. 2 shows the peak comparison among chromatograms of an aqueous solution of nalfurafine hydrochloride, Reference Example 13 (anhydrous crystalline fructose), Reference Example 14 (lactose) and Comparative Example 10 (sucrose).

As shown in FIG. 2, the tablets of Reference Examples 13 and 14 and Comparative Example 10 were analyzed by the analysis method using high performance chromatography to compare their chromatograms. In Reference Examples 13 and 14, no peak corresponding to the component amount of impurities of 1% or more based on the active ingredient was recognized within 20 to 75 minutes. Thus, we confirmed that a highly pure tableted pharmaceutical composition was obtained.

In sucrose, a peak corresponding to the component amount of impurities of 1% or more based on the active ingredient was recognized. In lactose and maltitol as well as monosaccharides, which are mannitol, glucose and anhydrous crystalline fructose, peaks appeared only slightly, which confirmed that a highly pure tableted pharmaceutical composition was obtained, and the effect was more pronounced in monosaccharides.

Example 1

Into a mortar, 97.895 parts of mannitol (PEARLITOL 200SD (registered trademark), manufactured by Roquette Japan K.K.) was weighed and charged. To these granules, a solution obtained by dissolving 0.005 parts of nalfurafine hydrochloride (manufactured by Toray Industries, Inc.), 0.1 parts of sodium thiosulfate hydrate (manufactured by Kokusan Chemical Co., Ltd.), and 1 part of hydroxypropyl cellulose whose 2% aqueous solution has a viscosity of 6 to 10 mPa·s at 20° C. (HPC-L, manufactured by Nippon Soda Co., Ltd.) in distilled water was added dropwise, mixed in the mortar and dried in a sample drier at 45° C. for 2 hours to obtain a granulated product. One part of magnesium stearate (manufactured by Taihei Chemical Industrial Co., Ltd.) was added to the granulated product and mixed in a bag. A hydraulic press was used at 100 kgf to pressurize 100 mg of the resulting granulated product to prepare a tablet (1 tablet) of 6 mm φ, which was used as Example 1. The weight of hydroxypropyl cellulose, which is the binder component of Example 1, is 1 weight % based on the tableted pharmaceutical composition, and 20,000 weight % based on nalfurafine hydrochloride.

The hardness of the tablet of Example 1 was measured with a hardness meter (manufactured by Okada Seiko Co., Ltd., PC-30). As shown in Table 6, the hardness of the tablet of Example 1 was 93 N, which was evaluated as ◎ referred to the formability criteria.

The extract extracted from 0.5 g of this granulated product with 5 mL of water was analyzed by HPLC, and the area values of the obtained peaks were compared to the total area value of the peaks within the analysis time, and the maximum component amount of impurities was calculated. As shown in Table 6, the maximum component amount of the impurities in Example 1 was 0.20%, which was evaluated as ○ referred to the high purity criteria.

Example 2

A tablet of 6 mm φ (1 tablet) was prepared in the same manner as in Example 1 except that the amount to be added of mannitol (PEARLITOL 200SD (registered trademark), manufactured by Roquette Japan K.K.) was changed to 93.895 parts, and the amount to be added of hydroxypropyl cellulose whose 2% aqueous solution has a viscosity of 6 to 10 mPa·s at 20° C. (HPC-L, manufactured by Nippon Soda Co., Ltd.) was changed to 5 parts. Specifically, 93.895 parts of mannitol (PEARLITOL 200SD (registered trademark), manufactured by Roquette Japan K.K.) was weighed and charged into a mortar. To these granules, a solution obtained by dissolving 0.005 parts of nalfurafine hydrochloride (manufactured by Toray Industries, Inc.), 0.1 parts of sodium thiosulfate hydrate (manufactured by Kokusan Chemical Co., Ltd.), and 5 parts of hydroxypropyl cellulose whose 2% aqueous solution has a viscosity of 6 to 10 mPa·s at 20° C. (HPC-L, manufactured by Nippon Soda Co., Ltd.) in distilled water was added dropwise, mixed in the mortar and dried in a sample drier at 45° C. for 2 hours to obtain a granulated product. One part of magnesium stearate (manufactured by Taihei Chemical Co., Ltd.) was added to the granulated product and mixed in a bag. A hydraulic press was used at 100 kgf to pressurize 100 mg of the resulting granulated product to prepare a tablet (1 tablet) of 6 mm φ, which was used as Example 2. Furthermore, the same measurement was carried out for the maximum component amount of impurities and the hardness of the tablet in Example 2. The weight of hydroxypropyl cellulose, which is the binder component of Example 2, is 5 weight % based on the tableted pharmaceutical composition, and 100,000 weight % based on nalfurafine hydrochloride.

As shown in Table 6, the maximum component amount of the impurities in Example 2 was 0.25%, which was evaluated as ○ referred to the high purity criteria. In addition, as shown in Table 6, the hardness of the tablet of Example 2 was 119 N, which was evaluated as ◎ referred to the formability criteria.

Example 3

Into a mortar, 93.895 parts of mannitol (PEARLITOL 200SD (registered trademark), manufactured by Roquette Japan K.K.) and 5 parts of maltitol (POWDER MABIT, manufactured by Hayashibara Co., Ltd.) were weighed and charged. To these granules, a solution obtained by dissolving 0.005 parts of nalfurafine hydrochloride (manufactured by Toray Industries, Inc.) and 0.1 parts of sodium thiosulfate hydrate (manufactured by KOKUSAN CHEMICAL Co., Ltd.) in distilled water was added dropwise, mixed in the mortar and dried in a sample drier at 45° C. for 2 hours to obtain a granulated product. One part of magnesium stearate (manufactured by Taihei Chemical Industrial Co., Ltd.) was added to the granulated product and mixed in a bag. A hydraulic press was used at 100 kgf to pressurize 100 mg of the resulting granulated product to prepare a tablet of 6 mm φ, which was used as Example 3. The weight of maltitol, which is the binder component of Example 3, is 5 weight % based on the tableted pharmaceutical composition, and 100,000 weight % based on nalfurafine hydrochloride.

The hardness of the tablet of Example 3 was measured with a hardness meter (manufactured by Okada Seiko Co., Ltd., PC-30). As shown in Table 6, the hardness of the tablet of Example 3 was 117 N, which was evaluated as ◎ referred to the formability criteria.

The extract extracted from 0.5 g of this granulated product with 5 mL of water was analyzed by HPLC, and the area values of the obtained peaks were compared to the total area value of the peaks within the analysis time, and the maximum component amount of impurities was calculated. As shown in Table 6, the maximum component amount of the impurities in Example 3 was 0.28%, which was evaluated as ○ referred to the high purity criteria.

Example 4

A tablet of 6 mm φ (1 tablet) was prepared in the same manner as in Example 3 except that the amount to be added of mannitol (PEARLITOL 200SD (registered trademark), manufactured by Roquette Japan K.K.) was changed to 78.895 parts, and the amount to be added of maltitol (POWDER MABIT, manufactured by Hayashibara Co., Ltd.) was changed to 20 parts. Specifically, 78.895 parts of mannitol (PEARLITOL 200SD (registered trademark), manufactured by Roquette Japan K.K.) and 20 parts of maltitol (Powder Mabit, manufactured by Hayashibara Co., Ltd.) were weighed and charged into a mortar. To these granules, a solution obtained by dissolving 0.005 parts of nalfurafine hydrochloride (manufactured by Toray Industries, Inc.) and 0.1 parts of sodium thiosulfate hydrate (manufactured by Kokusan Chemical Co., Ltd.) in distilled water was added dropwise, mixed in the mortar and dried in a sample drier at 45° C. for 2 hours to obtain a granulated product. One part of magnesium stearate (manufactured by Taihei Chemical Industrial Co., Ltd.) was added to the granulated product and mixed in a bag. A hydraulic press was used at 100 kgf to pressurize 100 mg of the resulting granulated product to prepare a tablet of 6 mm φ, which was used as Example 4. Furthermore, the same measurement was carried out for the maximum component amount of impurities and the hardness of the tablet in Example 4. The weight of maltitol, which is the binder component of Example 4, is 20 weight % based on the tableted pharmaceutical composition, and 400,000 weight % based on nalfurafine hydrochloride.

As shown in Table 6, the maximum component amount of the impurities in Example 4 was 0.60%, which was evaluated as ○ referred to the high purity criteria. In addition, as shown in Table 6, the hardness of the tablet of Example 4 was 183 N, which was evaluated as ◎ referred to the formability criteria.

Example 5

An experiment was conducted in the same manner as in Example 3 except that maltitol in Example 3 was changed to pullulan (Japanese Pharmacopoeia pullulan, manufactured by Hayashibara Co., Ltd.). Specifically, 93.895 parts of mannitol (PEARLITOL 200SD (registered trademark), manufactured by Roquette Japan K.K.) and 5 parts of pullulan (Japanese Pharmacopoeia pullulan, manufactured by Hayashibara Co., Ltd.) were weighed and charged into a mortar. To these granules, a solution obtained by dissolving 0.005 parts of nalfurafine hydrochloride (manufactured by Toray Industries, Inc.) and 0.1 parts of sodium thiosulfate hydrate (manufactured by Kokusan Chemical Co., Ltd.) in distilled water was added dropwise, mixed in the mortar and dried in a sample drier at 45° C. for 2 hours to obtain a granulated product. One part of magnesium stearate (manufactured by Taihei Chemical Industrial Co., Ltd.) was added to the granulated product and mixed in a bag. A hydraulic press was used at 100 kgf to pressurize 100 mg of the resulting granulated product to prepare a tablet of 6 mm φ, which was used as Example 5. Furthermore, the same measurement was carried out for the maximum component amount of impurities and the hardness of the tablet in Example 5. The weight of pullulan, which is the binder component of Example 5, is 5 weight % based on the tableted pharmaceutical composition, and 100,000 weight % based on nalfurafine hydrochloride.

As shown in Table 6, the maximum component amount of the impurities in Example 5 was 0.24%, which was evaluated as ○ referred to the high purity criteria. In addition, as shown in Table 6, the hardness of the tablet of Example 5 was 87 N, which was evaluated as ◎ referred to the formability criteria.

Example 6

An experiment was conducted in the same manner as in Example 4 except that maltitol in Example 4 was changed to pullulan (Japanese Pharmacopoeia pullulan, manufactured by Hayashibara Co., Ltd.). Specifically, 78.895 parts of mannitol (PEARLITOL 200SD (registered trademark), manufactured by Roquette Japan K.K.) and 20 parts of pullulan (Japanese Pharmacopoeia pullulan, manufactured by Hayashibara Co., Ltd.) were weighed and charged into a mortar. To these granules, a solution obtained by dissolving 0.005 parts of nalfurafine hydrochloride (manufactured by Toray Industries, Inc.) and 0.1 parts of sodium thiosulfate hydrate (manufactured by Kokusan Chemical Co., Ltd.) in distilled water was added dropwise, mixed in the mortar and dried in a sample drier at 45° C. for 2 hours to obtain a granulated product. One part of magnesium stearate (manufactured by Taihei Chemical Industrial Co., Ltd.) was added to the granulated product and mixed in a bag. A hydraulic press was used at 100 kgf to pressurize 100 mg of the resulting granulated product to prepare a tablet of 6 mm φ, which was used as Example 6. Furthermore, the same measurement was carried out for the maximum component amount of impurities and the hardness of the tablet in Example 6. The weight of pullulan, which is the binder component of Example 6, is 20 weight % based on the tableted pharmaceutical composition, and 400,000 weight % based on nalfurafine hydrochloride.

As shown in Table 6, the maximum component amount of the impurities in Example 4 was 0.50%, which was evaluated as ○ referred to the high purity criteria. As shown in Table 6, the hardness of the tablet of Example 4 was 161 N, which was evaluated as ◎ referred to the formability criteria.

Comparative Example 11

Into a mortar, 87.1464 parts of lactose (PHARMATOSE 200M (registered trademark), manufactured by DMV-Fonterra Excipients) and 8.75 parts of low-substituted hydroxypropyl cellulose (L-HPC) (LH-11, Shin-Etsu Chemical Co., Ltd.) were weighed and charged. To these granules, a solution obtained by dissolving 0.0036 parts of nalfurafine hydrochloride (manufactured by Toray Industries, Inc.), 0.1 parts of sodium thiosulfate hydrate (manufactured by Kokusan Chemical Co., Ltd.) and 3 parts of hydroxypropyl methylcellulose (HPMC 2910, manufactured by Shin-Etsu Chemical Co., Ltd.) in distilled water was added dropwise, mixed in the mortar and dried in a sample drier at 45° C. for 2 hours to obtain a granulated product. One part of magnesium stearate (manufactured by Taihei Chemical Industrial Co., Ltd.) was added to the granulated product and mixed in a bag. A hydraulic press was used at 100 kgf to pressurize 100 mg of the resulting granulated product to prepare a tablet (1 tablet) of 6 mm φ. The weight of hydroxypropyl cellulose, which is the binder component of Comparative Example 11, is 3 weight % based on the tableted pharmaceutical composition, and 83.333 weight % based on nalfurafine hydrochloride.

The hardness of the tablet of Comparative Example 11 was measured with a hardness meter (manufactured by Okada Seiko Co., Ltd., PC-30). As shown in Table 6, the hardness of the tablet of Comparative Example 11 was 46 N, which was evaluated as ○ referred to the formability criteria.

The extract extracted from 0.5 g of this granulated product with 5 mL of water was analyzed by HPLC, and the area values of the obtained peaks were compared to the total area value of the peaks within the analysis time, and the maximum component amount of impurities was calculated. Table 6 shows the effect of different binder components in Comparative Examples 6 to 9 and Reference Examples 8 to 10 on the formability of the tablet and on the purity of the tableted pharmaceutical composition. As shown in Table 6, the maximum component amount of the impurities in Comparative Example 11 was 15.59%, which was evaluated as x referred to the high purity criteria.

Figure 3:
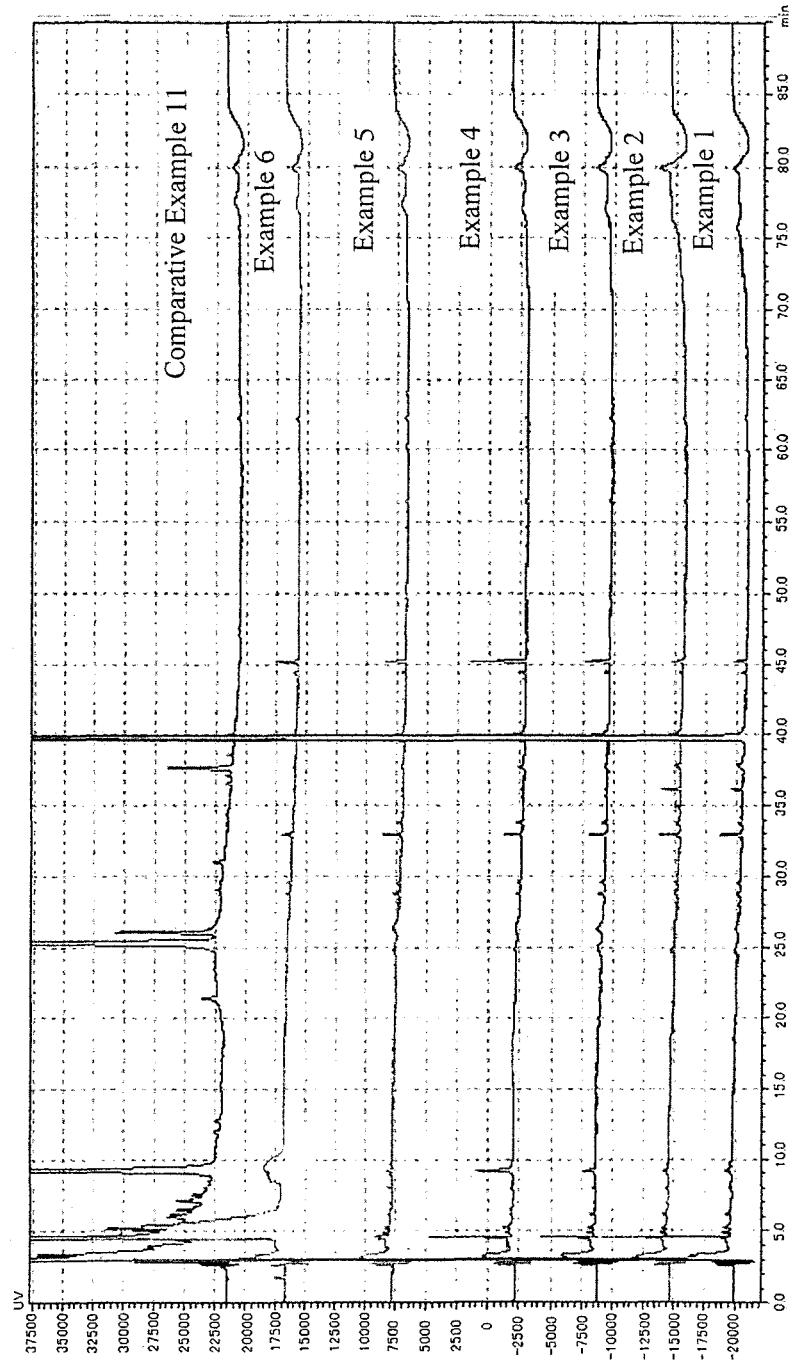
FIG. 3 shows the peak comparison among chromatograms of Examples 1 to 6 and Comparative Example 11.

Furthermore, as shown in FIG. 3, the tablets of Examples 1 to 6 were analyzed by the analysis method using high performance chromatography to compare their chromatograms. In all the Examples, no peak corresponding to the component amount of impurities of 1% or more based on the active ingredient was recognized within 20 to 75 minutes. Thus, we confirmed that highly pure tableted pharmaceutical compositions were obtained.

Demonstration with Tablets Containing the Active Ingredient

TABLE 6

|  | Example 1 | Example 2 | Example 3 | Example 4 | Example 5 | Example 6 | Comparative Example 11 |
|---|---|---|---|---|---|---|---|
| Nalfurafine hydrochloride (weight %) | 0.005 | 0.005 | 0.005 | 0.005 | 0.005 | 0.005 | 0.0036 |
| Mannitol (weight %) | 97.895 | 93.895 | 93.895 | 78.895 | 93.895 | 78.895 | — |
| Maltitol (weight %) | — | — | 5 | 20 | — | — | — |
| Pullulan (weight %) | — | — | — | — | 5 | 20 | — |
| HPC-L (weight %) | 1 | 5 | — | — | — | — | — |
| Lactose (weight %) | — | — | — | — | — | — | 87.1464 |
| HPMC2910 (weight %) | — | — | — | — | — | — | 3.0 |
| L-HPC (weight %) | — | — | — | — | — | — | 8.75 |
| Sodium thiosulfate (weight %) | 0.1 | 0.1 | 0.1 | 0.1 | 0.1 | 0.1 | 0.1 |
| Magnesium stearate (weight %) | 1 | 1 | 1 | 1 | 1 | 1 | 1 |
| Formability | ◎ (93N) | ◎ (119N) | ◎ (117N) | ◎ (183N) | ◎ (87N) | ◎ (161N) | ○ (46N) |
| High purity | ○ (0.20%) | ○ (0.25%) | ○ (0.28%) | ○ (0.60%) | ○ (0.24%) | ○ (0.50%) | X (15.59%) |

Formability criteria: ○ in the case of 40N or more and ◎ in the case of 50N or more.
High purity criteria: In the tableted pharmaceutical composition containing 5 μg of the active ingredient of Examples 1 to 6 and in the tableted pharmaceutical composition containing 3.6 μg of the active ingredient of Comparative Example 11, X in the case of more than 1%, ○ in the case of 1% or less, and ◎ in the case of 0.1% or less.

INDUSTRIAL APPLICABILITY

In a tableted pharmaceutical composition comprising nalfurafine hydrochloride or a pharmaceutically acceptable acid addition salt thereof, both of the assured formability and easy control of related substances can be achieved. By virtue of this, the detection accuracy of related substances improves and the measurement of a trace of related substances can be attained.

The invention claimed is:

1. A tableted pharmaceutical composition comprising nalfurafine or a pharmaceutically acceptable acid addition salt thereof; a binder component selected from the group consisting of maltose, maltitol, dextrin and pullulan; and a carrier,
   wherein said nalfurafine or a pharmaceutically acceptable acid addition salt thereof is contained in an amount of 0.1 to 10 μg, and
   the weight of said binder component is 100,000 to 2,000,000 weight % based on the weight of said nalfurafine or a pharmaceutically acceptable acid addition salt thereof and 5 to 20 weight % based on the total weight of the resulting pharmaceutical composition.

2. A tableted pharmaceutical composition comprising nalfurafine or a pharmaceutically acceptable acid addition salt thereof; a binder component containing hydroxypropyl cellulose whose 2% aqueous solution has a viscosity of greater than 5.9 mPa·s at 20° C.; and a carrier,
wherein said nalfurafine or a pharmaceutically acceptable acid addition salt thereof is contained in an amount of 0.1 to 10 μg, and
the weight of said binder component is 20,000 to 500,000 weight % based on the weight of said nalfurafine or a pharmaceutically acceptable acid addition salt thereof and 1 to 5 weight % based on the total weight of the resulting pharmaceutical composition.

3. The pharmaceutical composition according to claim 1, wherein the weight of said binder component is 100,000 to 400,000 weight % based on the weight of said nalfurafine or a pharmaceutically acceptable acid addition salt thereof.

4. The pharmaceutical composition according to claim 2, wherein the weight of said binder component is 20,000 to 100,000 weight % based on the weight of said nalfurafine or a pharmaceutically acceptable acid addition salt thereof.

5. The pharmaceutical composition according to claim 1, wherein said nalfurafine or a pharmaceutically acceptable acid addition salt thereof is contained in an amount of 1 to 5 μg.

6. The pharmaceutical composition according to claim 1, wherein said carrier is selected from the group consisting of mannitol, glucose, anhydrous crystalline fructose, lactose and maltitol.

7. A tablet composed of the pharmaceutical composition according to claim 1.

8. The pharmaceutical composition according to claim 2, wherein said nalfurafine or a pharmaceutically acceptable acid addition salt thereof is contained in an amount of 1 to 5 μg.

9. The pharmaceutical composition according to claim 3, wherein said nalfurafine or a pharmaceutically acceptable acid addition salt thereof is contained in an amount of 1 to 5 μg.

10. The pharmaceutical composition according to claim 4, wherein said nalfurafine or a pharmaceutically acceptable acid addition salt thereof is contained in an amount of 1 to 5 μg.

11. The pharmaceutical composition according to claim 2, wherein said carrier is selected from the group consisting of mannitol, glucose, anhydrous crystalline fructose, lactose and maltitol.

12. The pharmaceutical composition according to claim 3, wherein said carrier is selected from the group consisting of mannitol, glucose, anhydrous crystalline fructose, lactose and maltitol.

13. The pharmaceutical composition according to claim 4, wherein said carrier is selected from the group consisting of mannitol, glucose, anhydrous crystalline fructose, lactose and maltitol.

14. The pharmaceutical composition according to claim 5, wherein said carrier is selected from the group consisting of mannitol, glucose, anhydrous crystalline fructose, lactose and maltitol.

15. A tablet composed of the pharmaceutical composition according to claim 2.

16. A tablet composed of the pharmaceutical composition according to claim 3.

17. A tablet composed of the pharmaceutical composition according to claim 4.

18. A tablet composed of the pharmaceutical composition according to claim 5.

19. A tablet composed of the pharmaceutical composition according to claim 6.

* * * * *